(12) United States Patent
Matsumoto et al.

(10) Patent No.: US 6,372,944 B1
(45) Date of Patent: Apr. 16, 2002

(54) LIQUID WITHDRAWING TRAY FOR PURIFICATION COLUMN, PURIFICATION COLUMN, AND METHOD FOR PURIFICATION

(75) Inventors: Hajime Matsumoto; Takeshi Nishimura; Yukihiro Matsumoto; Sei Nakahara; Misao Inada, all of Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/667,283

(22) Filed: Sep. 22, 2000

(30) Foreign Application Priority Data

Sep. 29, 1999 (JP) ............................................. 11-277199

(51) Int. Cl.⁷ ............................................. C07C 51/42
(52) U.S. Cl. ....................... 562/600; 202/158; 203/100; 261/114.1
(58) Field of Search ....................... 562/600; 202/158; 203/100; 261/114.1

(56) References Cited

U.S. PATENT DOCUMENTS

| 5,308,451 A | 5/1994 | Carland ....................... 202/158 |
| 5,470,478 A | 11/1995 | Leva ........................... 210/634 |
| 5,902,460 A | 5/1999 | Gerhold ........................ 203/99 |
| 6,228,227 B1 * | 5/2001 | Herbst et al. .................. 203/59 |

FOREIGN PATENT DOCUMENTS

| DE | 4231081 A | 4/1993 | ............ B01D/3/14 |
| FR | 2103267 A | 4/1972 | ............ B01D/3/00 |
| GB | 740764 A | 11/1955 | |
| JP | A-9-227445 | 9/1997 | |

OTHER PUBLICATIONS

Kister, Henry Z., Distillation Operation, pp. 103–118.

* cited by examiner

*Primary Examiner*—Robert J. Popovics
(74) *Attorney, Agent, or Firm*—Mathews, Collins, Shepherd & Gould, P.A.

(57) ABSTRACT

In the purification of an easily polymerizable compound such as (meth)acrylic acid by the use of a purification column adapted to withdraw a liquid from the middle portion of the column, a novel liquid withdrawing tray adapted to prevent the compound from polymerization effectively and permit the purification to be stably performed for a long time, a purification column using this tray, and a method for purifications using this purification column are provided. The liquid withdrawing tray for the purification column is composed of a liquid receiving plate and a liquid withdrawing tube for withdrawing the liquid from the liquid receiving plate.

3 Claims, 5 Drawing Sheets

LIQUID WITHDRAWING TRAY FOR PURIFICATION COLUMN, PURIFICATION COLUMN, AND METHOD FOR PURIFICATION

BACKGROUND OF THE INVENTION

1. Field of the Invention

This invention relates to a liquid withdrawing tray for a purification column, a purification column, and a method for purification. More particularly, it relates to a tray for withdrawing a liquid from a middle portion or middle level of a purification column, a purification column furnished with the tray, and a method for purification an easily polymerizable compound such as (meth)acrylic acid by the use of the purification column.

2. Description of the Prior Art

As a method for production of acrylic acid and esters thereof, the method by oxidizing propylene and/or acrolein with a molecular oxygen-containing gas in vapor phase, recovering a reaction product gas thus obtained with a solvent, and subjecting a reaction product-containing solution thus obtained purification in a purification column to obtain purified acrylic acid or esters thereof (JP-A-9-227445).

In the purification column, such operations as withdrawing reflux liquid in the column from the middle portion, generally the middle level, of the column for the purpose of withdrawing an intermediate product, and cooling or heating the reflux liquid are routine. Then, for the purpose of withdrawing the liquid from the middle portion of the purification column, the chimney tray which is composed of a vapor conduit (gas riser), an umbrella covering the conduit, and a liquid withdrawing tube has been popularly used (refer, for example, to Henry Z. Kister, "Distillation Operation," pp. 102–116 [published in 1990 by McGraw Hill, Inc.]). The chimney tray which is concurrently provided with a vapor conduit and a liquid withdrawing tube is also available for the purpose of the withdrawal of interest.

In purification of such an easily polymerizable compound as (meth)acrylic acid, the measure taken to polymerize the easily polymerizable compound is important for operating the purification column stably. For inhibiting this polymerization, the practice of adding such a polymerization inhibitor as phenothiazine, hydroquinone, or methoquinone has been in vogue.

When the purification column provided with the chimney tray is used in purifying the easily polymerizable compound, however, the polymerization of the compound occurs throughout the entire chimney tray inclusive of the vapor conduit and the umbrella in spite of the use of the polymerization inhibitor and the polymer brings the problem of clogging the chimney tray and preventing it from being stably operated for a long time. Then, in the case of the chimney tray provided concurrently with a vapor conduit and a liquid withdrawing tube, since the descending liquid comes into counterflow contact with the vapor in motion at a relatively high speed, this vapor entrains liquid splash to the upper part of the purification column and impairs the separating effect of the purification column. This impairment possibly results in increasing the content of impurities in the target product of purification obtained via the top of the column.

An object of this invention, therefore, is to provide a novel liquid withdrawing tray for the purification column, a purification column utilizing the tray, and a method for purification.

Another object of this invention is to provide a tray for withdrawing the liquid from the middle portion or middle level of the purification column, a purification column provided with the tray, and a method for purification such an easily polymerizable compound as (meth)acrylic acid by the use of this purification column.

Still another object of this invention is to provide, in purification such an easily polymerizable compound as (meth)acrylic acid, a novel liquid withdrawing tray adapted to allow effective prevention of the polymerization and enable the purification to be performed stably for a long time, a purification column provided with the tray, and a method for purifying the easily polymerizable compound by using the purification column.

SUMMARY OF THE INVENTION

The objects mentioned above are accomplished by the following items (1)–(10).

(1) A liquid withdrawing tray for a purification column, comprising a liquid receiving plate and a liquid withdrawing tube communicating with the liquid receiving plate and serving the purpose of withdrawing the liquid.

(2) A tray set forth in (1) above, wherein the receiving plate has the shape of a funnel.

(3) A tray set forth in (1) or (2) above, wherein the liquid receiving plate is provided in the upper outer periphery thereof with notches.

(4) A tray set forth in any one of (1)–(3) above, wherein the angle of the downward slope of the liquid withdrawing tube from the horizontal direction is in the range of 0.5°–80°.

(5) A purification column provided in the column interior thereof with a liquid withdrawing tray set forth in any one of (1)–(4) above.

(6) A purification column set forth in (5) above, wherein the largest cross sectional area, S1, of the liquid withdrawing tray is in the range of 10–90% of the cross sectional area, S2, of the purification column.

(7) A purification column set forth in (5) or (6) above, wherein the liquid receiving plate is provided thereunder with at least one spray nozzle for spraying the lower side of the liquid receiving plate with a liquid.

(8) A purification column set forth in any one of (5)–(7) above, wherein the liquid receiving plate is provided thereover with at least one liquid injecting nozzle for injecting a liquid into the liquid surface in the liquid receiving plate.

(9) A method for purifying an easily polymerizable compound, which comprises effecting the purification by the use of a purification column set forth in any one of (5)–(8) above.

(10) A method set forth in (9) above, wherein the easily polymerizable compound is at least one member selected from the group consisting of (meth)acrylic acid and esters thereof.

In the purification column, the polymerization inhibitor is present mainly in the liquid phase and hardly ever in the gas phase. When the vapor in the gas phase condenses in the dry part of the interior of the purification column, therefore, the condensate readily polymerizes because it is exposed in a state destitute of the polymerization inhibitor at a relatively high temperature in the purification column.

In the case of the chimney tray, the lower (reverse) surface of the umbrella covering the vapor conduit is not always kept wet with the condensate and, therefore, is possibly suffered to permit the appearance of a dry part. More often than not, the polymerization occurs in the dry part under the umbrella.

The study further continued has brought a discovery that the use of a funnel-shaped tray devoid of an umbrella in the place of the conventional chimney tray deprives the tray surface of the dry part and consequently permits effective prevention of the occurrence of the polymerization. The present invention has been perfected on the basis of this knowledge.

By adopting the liquid withdrawing tray of this invention and using the purification column provided with this tray in purifying an easily polymerizable compound such as (meth) acrylic acid, for example, it is possible to effectively prevent polymerization in the tray of easily polymerizable compounds.

EXPLANATION OF THE PREFERRED EMBODIMENTS

Now, the preferred embodiments of this invention will be explained below with reference to the accompanying drawings.

Figure 1:
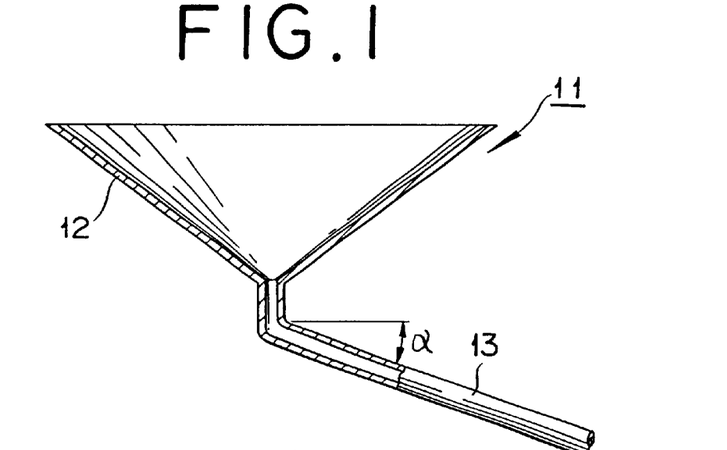
FIG. 1 is a cross section illustrating one preferred embodiment of the liquid withdrawing tray according to this invention.

FIG. 1 is a cross section illustrating one preferred embodiment of the liquid withdrawing tray according to this invention. A liquid withdrawing tray 11 is composed of a liquid receiving plate 12 and a liquid withdrawing tube 13 communicating with the bottom part of the liquid receiving plate and serving the purpose of withdrawing the liquid in the liquid receiving plate out of a purification column (not shown). The lateral shape (the shape of longitudinal cross section) of this liquid receiving plate 12 does not need to be particularly discriminated but has only to be capable of accommodating the liquid in the purification column (not shown) and allowing the liquid to overflow the liquid receiving plate 12 in the proximity of the upper end part thereof, wet the lower lateral face of the tray, and prevent the lower lateral face from producing a dry part. Generally, this lateral shape is preferred to resemble a funnel as illustrated in FIG. 1 and the plan view of the liquid receiving plate 12 is a circle, for example. The liquid withdrawing tube 13 in this case is so constructed as to extend in the perpendicular direction from the lowermost part of the liquid receiving plate 12, begin to slope down at a point halfway along the entire length thereof, and communicate with the exterior of the purification column (not shown).

The plan shape of the liquid receiving plate 12 has no particular restriction either but has only to be capable of being set in the purification column. As typical examples of the plan shape, a circle, a semicircle, an ellipsis, a square, and a broken circle may be cited. Among other shapes mentioned above, the circle is used particularly advantageously.

FIGS. 2–8 are schematic cross sections illustrating preferred embodiments of the liquid withdrawing tray using the same liquid receiving plates as the funnel-shaped liquid receiving plate illustrated in FIG. 1.

Figure 2:
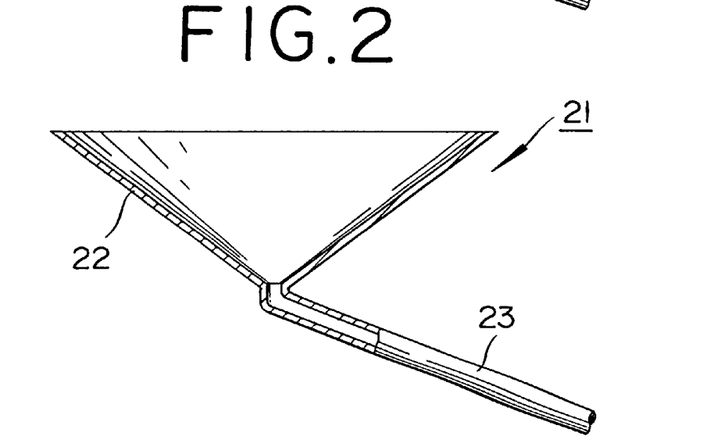
FIG. 2 is a cross section illustrating another preferred embodiment of the liquid withdrawing tray according to this invention.

Specifically, in a liquid withdrawing tray 21 illustrated in FIG. 2, a liquid receiving plate 22 has a funnel-shaped longitudinal cross section similarly in the embodiment of FIG. 1 and a liquid withdrawing tube 23 descends in an oblique direction from the bottom part of the liquid receiving plate 22.

Figure 3:
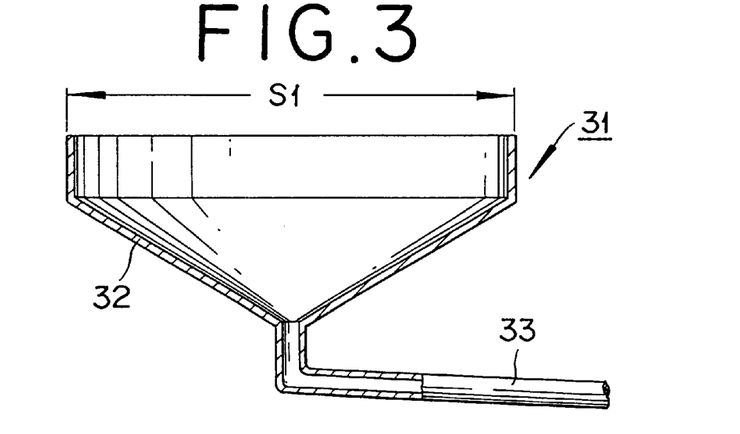
FIG. 3 is a cross section illustrating still another preferred embodiment of the liquid withdrawing tray according to this invention.

In a liquid withdrawing tray 31 illustrated in FIG. 3, a liquid receiving plate 32 has a cylindrical shape containing a converging part in the lower portion thereof. From the bottom part of the liquid receiving plate 32, a liquid withdrawing tube 33 descends and turns in a substantially horizontal direction at a point halfway along the entire length thereof and communicates with the exterior.

Figure 4:
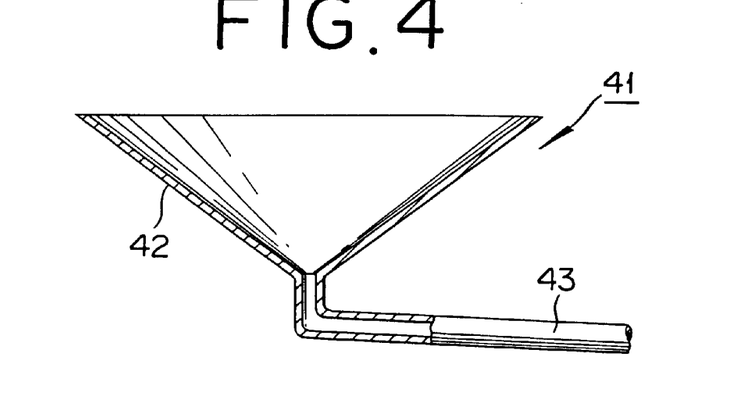
FIG. 4 is a cross section illustrating yet another preferred embodiment of the liquid withdrawing tray according to this invention.

In a liquid withdrawing tray 41 illustrated in FIG. 4, a liquid receiving plate 42 is shaped like a funnel similarly in the embodiment of FIG. 1 and a liquid withdrawing tube 43 descends from the bottom part of the liquid receiving plate 42 and turns in a substantially horizontal direction at a point halfway along the entire length thereof and communicates with the exterior similarly in the embodiment of FIG. 3.

Figure 5:
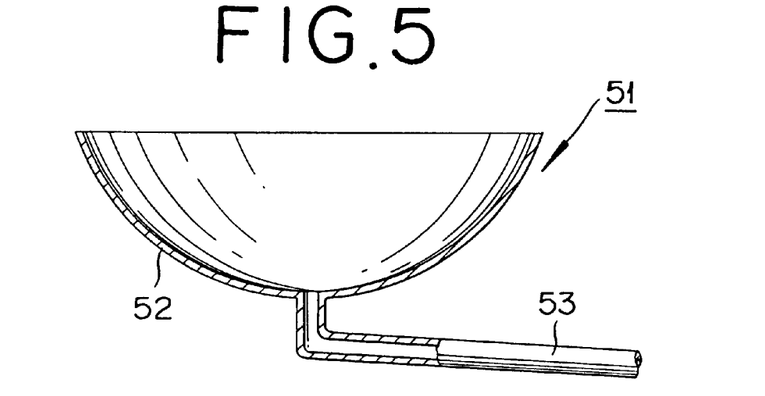
FIG. 5 is a cross section illustrating another preferred embodiment of the liquid withdrawing tray according to this invention.

In a liquid withdrawing tray 51 illustrated in FIG. 5, a liquid receiving plate 52 is shaped like a bowl and a liquid withdrawing tube 53 is similar to the liquid withdrawing tubes of FIG. 3 and FIG. 4.

Figure 6:
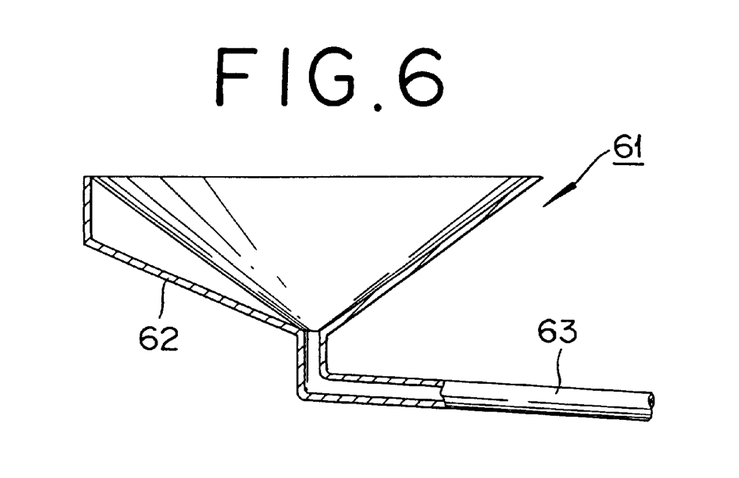
FIG. 6 is a cross section illustrating still another preferred embodiment of the liquid withdrawing tray according to this invention.
Figure 7:
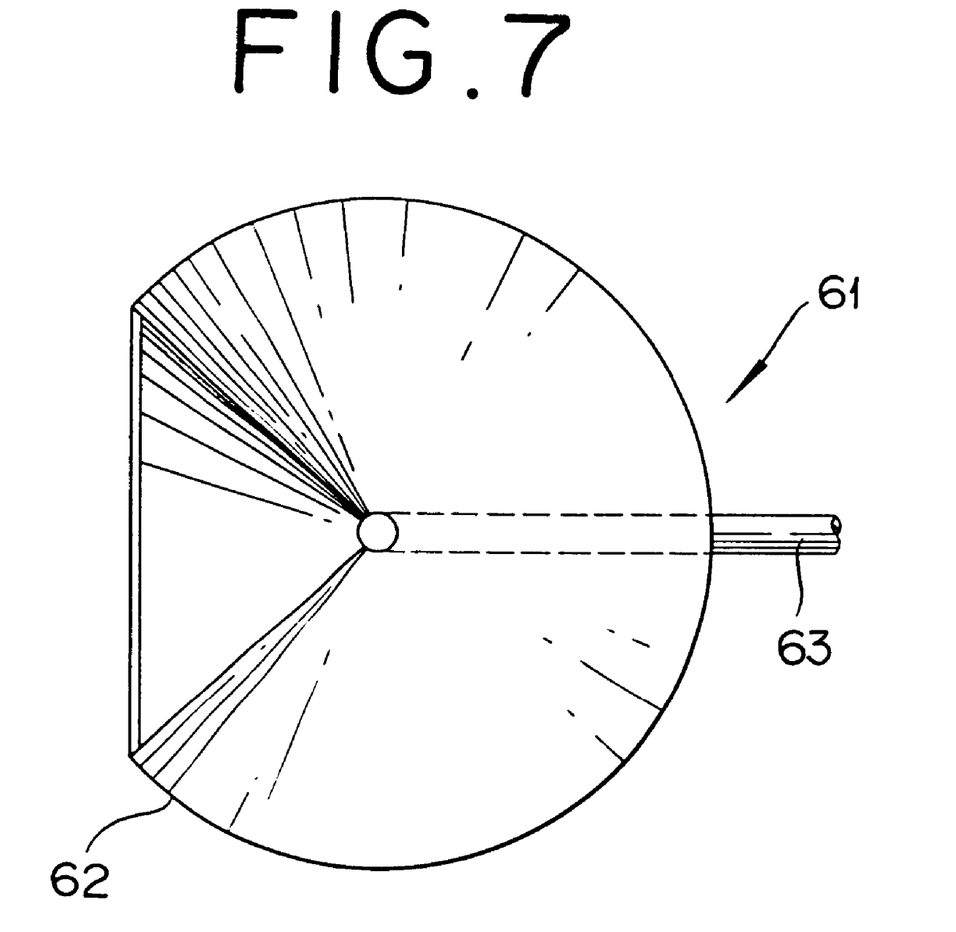
FIG. 7 is a plan view of the liquid withdrawing tray shown in FIG. 6.

A liquid withdrawing tray 61 illustrated in FIG. 6 is constructed by providing a liquid withdrawing tube 63 similar to those of FIG. 3–FIG. 5 for a liquid receiving plate 62 comprising one side inclined from a perpendicular plane at a point halfway along the entire length thereof, the another side inclined from the upper through the lower end thereof (See FIG. 7).

Figure 8:
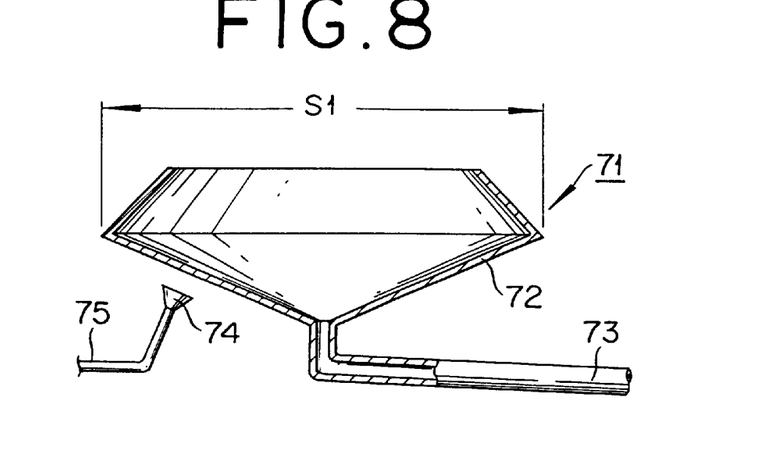
FIG. 8 is a cross section illustrating yet another preferred embodiment of the liquid withdrawing tray according to this invention.

In a liquid withdrawing tray 71 illustrated in FIG. 8, a liquid receiving plate 72 is shaped like a pot having a narrow opening and a liquid withdrawing tube 73 is similar to those of FIG. 3–FIG. 6. Then, the liquid receiving plate 72 is provided below the lower lateral side thereof with at least one spray nozzle 74 for spraying a liquid to the lower lateral side thereof, preferably a plurality of such spray nozzles spaced by an equal interval, to ensure the wetting of the lower lateral side. This liquid receiving plate 72 communicates with a liquid supply conduit 75.

Figure 9:
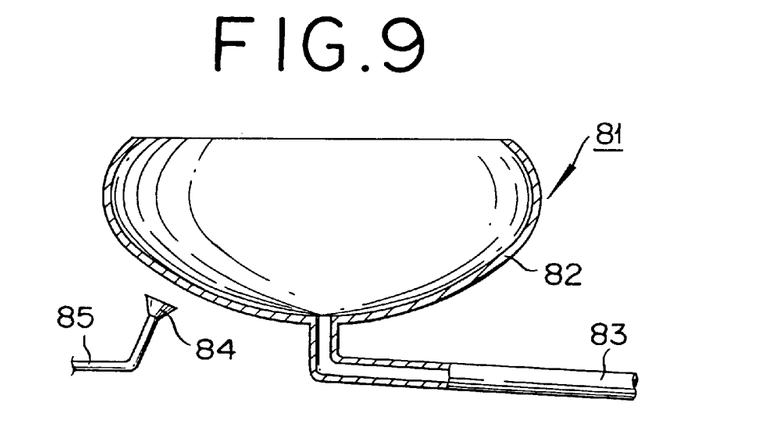
FIG. 9 is a cross section illustrating another preferred embodiment of the liquid withdrawing tray according to this invention.

In a liquid withdrawing tray 81 illustrated in FIG. 9, a liquid receiving plate 82 is shaped like a wine glass having a narrow opening and a liquid withdrawing tube is similar to those of FIG. 3–FIG. 8. Then, the liquid receiving plate 82 is provided below the lower lateral side thereof with at least one spray nozzle 84 for spraying a liquid to the lower lateral side thereof, preferably a plurality of such spray nozzles spaced by an equal interval, to ensure the wetting of the lower lateral side. This liquid receiving plate 82 communicates with a liquid supply conduit 85.

Above mentioned Figures show embodiments of funnel type liquid receiving plate, and the funnel type means a liquid receiving plate having a tapered portion at least one portion of the bottom. The liquid in the liquid receiving plate flows down smoothly without storage, so polymerization of the liquid is inhibited.

Figure 10:
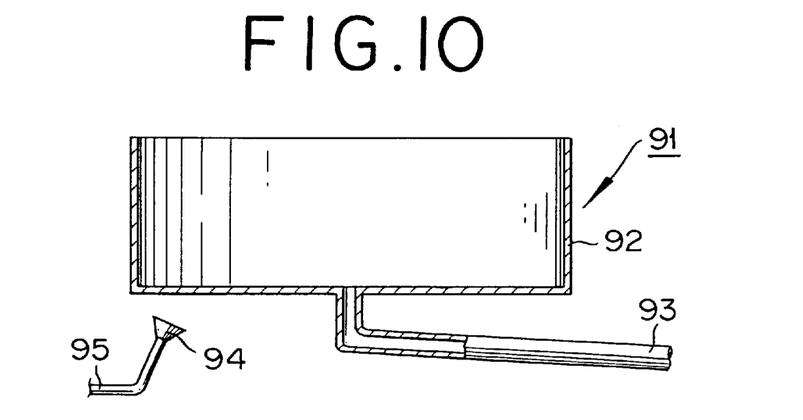
FIG. 10 is a cross section illustrating still another preferred embodiment of the liquid withdrawing tray according to this invention.

FIG. 10 shows an embodiment of a dish type liquid receiving plate and the liquid receiving plate 92 has the shape of a cylinder or a square cup and a liquid withdrawing tube 93 is similar to those of FIG. 3–FIG. 9. Then, the liquid receiving plate 92 is provided below the lower lateral side thereof with at least one spray nozzle 94 for spraying a liquid to the lower lateral side thereof, preferably a plurality of such spray nozzles spaced by an equal interval, to ensure the wetting of the lower lateral side. This liquid receiving plate 92 communicates with a liquid supply conduit 95.

In the liquid receiving plates illustrated in FIG. 1–FIG. 10, those illustrated in FIG. 1–FIG. 6 are used particularly advantageously because their lower lateral sides are wetted throughout with the liquid overflowing the liquid receiving plates near the upper ends thereof and are substantially incapable of producing a dry part. They also enable their pertinent purification columns to effect the expected separation with an exalted efficiency because they reduce the entrainment of liquid splash to the upper parts of the purification columns.

The liquid receiving plates illustrated in FIG. 8–FIG. 10, for the purpose of ensuring the wetting of the lower lateral sides thereof, may be provided with at least one spray nozzle 74 for spraying the liquid or a plurality of such spray nozzles spaced with an equal interval. As the liquid used for spraying, it is advantageous to withdraw the liquid in the liquid receiving plate through the liquid withdrawing tube and circulate it to the spray nozzle because the use of this liquid in this manner has only sparing effect to bear on the material balance within the purification column.

The liquid withdrawing tube is commended to be inclined downward from the horizontal direction with an angle, (refer to FIG. 1), in the range of 0.5°–80°, preferably 1°–70°, and particularly preferably 2°–40°, lest the liquid should remain on the surface of the liquid withdrawing tube during a suspension of the operation of the purification column. If this angle is less than 0.50, the shortage will be at a disadvantage in suffering the liquid to remain readily because of insufficient descent of the liquid. Conversely, if the angle exceeds 80°, the excess will be at a disadvantage in the fact that a certain distance for a height direction in the column is required until the liquid is discharged, and as a result storage time in the gas phase becomes long, so the gas is apt to polymerize in the gas phase.

Figure 11:
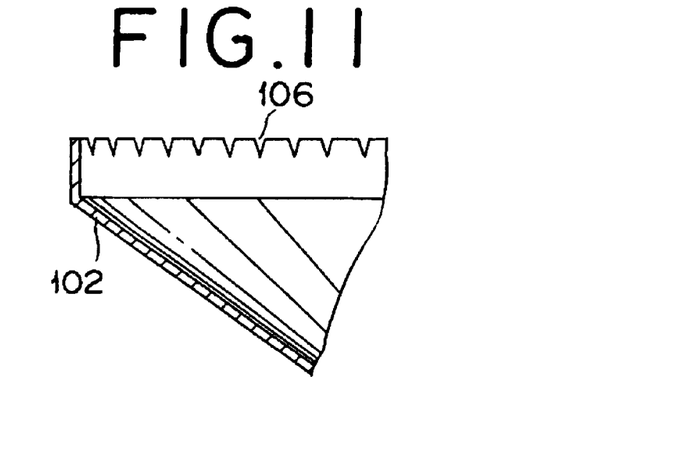
FIG. 11 is a partial side view illustrating one preferred embodiment of the liquid receiving plate in the liquid withdrawing tray according to this invention, wherein the plate is provided in the lateral face part thereof with notches.

The liquid withdrawing tray according to this invention is referred to be provided in the outer peripheral edge thereof with notches so as to promote the overflow of the liquid from the liquid receiving plate and keep the lateral side of the tray wet throughout the surface. FIG. 11 is a partially longitudinal cross section of a liquid receiving plate 102 which is provided with notches 106. Though the intervals between the notches and the widths and the largest depths of the notches are not generally definite because they are variable as with the size of the liquid receiving plate, the intervals between the notches (the distances between the bottom parts of the adjacent notches) are preferred to be in the range of 2–100 mm, preferably 5–50 mm, the widths of the notches to be in the range of 2–100 mm, preferably 5–50 mm, and the largest depths of the notches to be in the range of 2–100 mm, preferably 5–50 mm.

Incidentally, the shape of such notches does not need to be particularly limited and may be properly selected as from among a triangle (V-shape), a square, and a semicircle.

Figure 12:
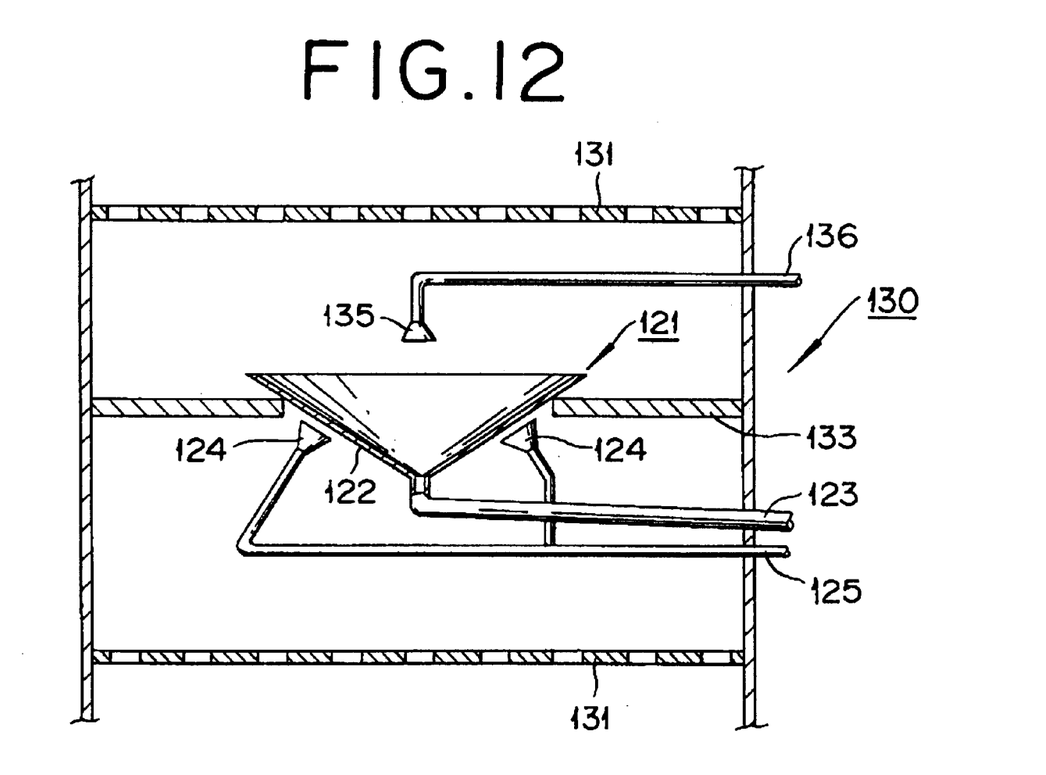
FIG. 12 is a partial cross section illustrating one preferred embodiment of the purification column of this invention provided with the liquid withdrawing tray.

FIG. 12 is an explanatory cross section of the purification column of this invention which is furnished with the liquid withdrawing tray mentioned above. Specifically, in a shelf type purification column 130 provided with a tray 131, a liquid withdrawing tray 121 provided with a liquid receiving plate 122 having a liquid withdrawing tube 123 connected to the bottom part thereof is supported by a liquid withdrawing tray-supporting plate 133.

As regards the size of the liquid withdrawing tray, the largest cross section (such as the area denoted by the reference numeral S1 in FIG. 3 and FIG. 8) is properly in the range of 10–90%, preferably 20–80%, of the cross section (S2) of the purification column. That is, the quotient of S1/S2 (×100) is preferred to fall in the range mentioned above. If the quotient exceed 90%, the excess will be at a disadvantage in increasing the pressure loss due to a decrease in the vapor flow path and tending to induce the entrainment of liquid splash due to an increase in the linear velocity of the vapor. Conversely, if the quotient is less than 10%, the shortage will be at a disadvantage in preventing the purposes of such actions as mixing, cooling, heating, and drawal of an intermediate product from being fully attained.

Part of the liquid received in the liquid withdrawing tray 121 is withdrawn in a prescribed unit volume from the purification column and the remainder thereof is left overflowing the tray 121 across the upper edge thereof. For the purpose of enabling the liquid to overflow the tray 121, it suffices to fix the amount of the liquid to be withdrawn to the exterior in the range of 5–80%, preferably 20–70%, of the amount of the reflux liquid in the column. The overflowing liquid keeps falling into the tray laid beneath while wetting the lower lateral side of the liquid withdrawing tray 121. By the reflux liquid containing the polymerization inhibitor, the lateral side of the liquid withdrawing tray 121 is kept wet and protected against polymerization. This overflow is promoted by the provision of the notches mentioned above.

For the purpose of effectively preventing the polymerization, the purification column may be provided with spray nozzles 124 adapted to spray part of the liquid withdrawn from the purification column against the lower lateral side of the tray 121. The nozzles communicate with a liquid supply conduit 125. Besides or simultaneously with the spray nozzles 124, the purification column may be provided with at least one liquid injection nozzle 135 adapted to inject the liquid into the liquid surface in the liquid withdrawing tray 121. This nozzle communicates with a liquid supply conduit 136. By injecting the liquid through this liquid injecting nozzle 135, it is made possible to keep the liquid in the liquid receiving plate stirred and prevent the liquid from stagnating and inducing polymerization. Incidentally, a spray nozzle is advantageously used as the liquid injection nozzle 135. When a separate feed liquid is simultaneously sprayed, the efficiency of separation is improved because the mixing of the reflux liquid in the column with the feed liquid is promoted.

When the liquid withdrawing tray in accordance with the present invention is used, in the purification column for the easily polymerizable compound, it is useful for the following objects. In a system where polymer generates, it is possible to discharge the liquid from the column, to separating a polymer by a solid-liquid separator and to return only the liquid into the column. Further, when a liquid composition between a reflux liquid in the column and a fed liquid is considerably different or the reflux liquid has two liquid phases, polymerization in the column can be inhibited by mixing uniformly. Furthermore, it becomes possible to inhibit the polymerization and continue the reaction by withdrawing the liquid in the column, adding the polymerization inhibitor and a reaction product, and returning it to the tray.

The method of this invention for the purification of an easily polymerizable compound can be implemented in an ordinary way except that the use of the purification column mentioned above. In this specification, the "purification" means distillation (rectification), stripping and absorption, and the "purification column" means distillation (rectification) column, stripper and absorber.

The liquid withdrawing tray and the purification column in accordance with this invention are used particularly advantageously in handling an easily polymerizable compound. The easily polymerizable compounds include (meth) acrylic acid and esters thereof. As typical examples of the compound, alkyl esters having alkyl groups of 1–8 carbon atoms such as methyl esters, ethyl esters, n-propyl esters, isopropyl esters, n-butyl esters, n-hexyl esters, and 2-ethylhexyl esters, cycloalkyl esters such as cyclohexyl esters, hydroxyalkyl esters of 2–3 carbon atoms such as 2-hydroxyethyl esters, 2-hydroxypropyl esters, and 3-hydroxypropyl esters, and alkyl or dialkylaminoalkyl esters such as methylaminoethyl esters, ethylaminoethyl esters, dimethylaminoethyl esters, and diethylaminoethyl esters may be cited. These compounds may be used for purification either singly or in the form of a mixture or a in the form of a solution containing them.

Now, this invention will be described more specifically below with reference to working examples.

EXAMPLE 1

A funnel-shaped liquid withdrawing tray fulfilling the following particulars and illustrated in FIG. 1 was installed between the $15^{th}$ and the $16^{th}$ shelf of a distillation column made of stainless steel (SUS 304) having an inside diameter of 1500 mm and containing a total of 50 shelves.

Diameter of the uppermost part (outer peripheral edge): 1100 mm

Cross section of tray/cross section of column (S1/S2): 0.54

Notches in the outer peripheral edge: V notches 10 mm in width, 10 mm in pitch, and 10 mm in depth Inclination ($\alpha$) of withdrawing tube: 1°

The distillation column mentioned above was kept supplied with acrylic acid containing maleic acid as impurity at a concentration of 0.8% by weight at a feed rate of 9 tones per hour and a continuous distillation was operated under the conditions of 0.6 of reflux ratio, 35 mmHg of working pressure, and 63° C. or working temperature. The liquid withdrawn to the exterior from the funnel-shaped liquid withdrawing tray was sprayed on the lateral side of the tray and the liquid surface respectively at a rate of 1 ton per hour.

During the course of the distillation, phenothiazine as a polymerization inhibitor was added to the feed liquid to the distillation column in an amount calculated to account for a concentration of 100 ppm. A gas containing oxygen was continuously supplied in a prescribed amount to the interior of the distillation column via the bottom thereof.

This apparatus was used to continue the distillation for 1 month. During this time, the distillate from the column top was found to contain maleic acid as an impurity at a concentration of 0.1% by weight. When the interior of the column was visually inspected after 1 month's operation, the amount of a polymer formed in the vicinity of the funnel-shaped withdrawing tray inclusive of the liquid withdrawing tube was found to be about 1 kg.

EXAMPLE 2

Continuous distillation was carried out by following the procedure of Example 1 while omitting the spray of the liquid to the lateral side of the funnel-shaped liquid withdrawing tray.

When the interior of the column was visually inspected after 1 month's continuous distillation, the amount of a polymer formed in the vicinity of the funnel-shaped withdrawing tray inclusive of the liquid withdrawing tube was found to be about 1.2 kg.

EXAMPLE 3

Continuous distillation was carried out by following the procedure of Example 1 while using a funnel-shaped liquid withdrawing tray containing no notch in the outer peripheral edge (with no other change).

When the interior of the column was visually inspected after 1 month's continuous distillation, the amount of a polymer formed in the vicinity of the funnel-shaped withdrawing tray inclusive of the liquid withdrawing tube was found to be about 1.2 kg.

EXAMPLE 4

Continuous distillation was carried out by following the procedure of Example 1 while using a funnel-shaped liquid withdrawing tray having no inclination in a liquid withdrawing tube ($\alpha=0$) (with no other change).

When the interior of the column was visually inspected after 1 month's continuous distillation, the amount of a polymer formed in the vicinity of the funnel-shaped withdrawing tray inclusive of the liquid withdrawing tube was found to be about 1.1 kg.

Control 1

Continuous distillation was carried out by following the procedure of Example 1 while using a chimney tray (cross section of tray/cross section of column=0.56, equivalent to a funnel-shaped liquid withdrawing tray measuring 1100 mm in inside diameter) provided with a vapor conduit 1000 mm in diameter in the place of the funnel-shaped liquid withdrawing tray.

During the 1 month's continued operation, the distillate emanating from the column top was found to contain maleic acid as an impurity at a concentration of 0.2% by weight. When the interior of the column was visually inspected after 1 month's continuous purification, the amount of a polymer formed in the vicinity of the chimney tray inclusive of the liquid withdrawing tube was found to be about 3 kg.

The results of the examples 1–4 and the control 1 are collectively shown in Table 1.

TABLE 1

|  |  | Example 1 | Example 2 | Example 3 | Example 4 | Control 1 |
|---|---|---|---|---|---|---|
| Inside diameter of distillation column | mm | 1500 | ← | ← | ← | ← |
| Number of shelves |  | 50 | ← | ← | ← | ← |
| Shelves used for intermediate extraction |  | 15~16 | ← | ← | ← | ← |
| Liquid withdrawing tray |  | funnel type | ← | ← | ← | riser type |
| Inside diameter of tray | mm | 1100 | ← | ← | ← | 1100 mm |
| Working pressure | mmHg | 35 | ← | ← | ← | ← |
| Working temperature | ° C. | 63 | ← | ← | ← | ← |
| Spray of lateral side of tray |  | yes | no | yes | ← | — |
| Notch |  | yes | ← | no | yes | ← |
| Inclination of withdrawing nozzle |  | yes | ← | ← | no | yes |
| Maleic acid contained in feed liquid to distillation column | Wt % | 0.8 | ← | ← | ← | ← |
| Polymerization inhibitor (phenothiazine) (After completion of 1 month's continued operation) | ppm | 100 | ← | ← | ← | ← |
| Maleic acid in distillate | Wt % | 0.1 | ← | ← | ← | 0.2 |
| Polymer in column | kg | 1 | 1.2 | 1.2 | 1.1 | 3 |

Comparison of the results of the working examples and those of the control reveals that the use of the liquid withdrawing tray of this invention permitted prevention of polymerization and allowed improvement in the efficiency of separation in the distillation column.

The entire disclosure of Japanese Patent Application No. 11-277199 filed on Sept. 29, 1999 including specification, claims and summary are incorporated therein by reference in its entirely.

What is claimed is:

1. In the purification of a polymerizable compound, the improvement in reducing the buildup of polymers or one or more polymerized compounds which comprises:

a) introducing into a distillation column a fluid, at least one component of which is a polymerizable compound;

b) passing the fluid over a liquid withdrawing tray disposed within the distillation column and having a concave liquid receiving plate with a liquid withdrawing tube communicating between the liquid receiving plate and the exterior of the distillation column, the liquid receiving plate having an open end that defines an upper outer periphery and a lower lateral surface opposed to the open end, the cross sectional area of the liquid withdrawing tray being less than the interior cross sectional area of the distillation column and disposed transverse to the longitudinal axis of the distillation column;

c) removing a portion of the fluid to the exterior of the distillation column by the liquid withdrawing tube; and d) permitting that portion of the fluid not withdrawn by the liquid withdrawing tube to the exterior of the distillation column to overflow the liquid receiving tray and coat the exterior surfaces of the liquid receiving tray and the liquid withdrawing tube.

2. The method of claim 1 where the polymerizable compound is at least one member selected from the group consisting of acrylic acid, methacrylic acid and its esters thereof.

3. The method of claim 1 where the purification of the fluid is performed continuously in the distillation column.

* * * * *